(12) United States Patent
Dalrymple et al.

(10) Patent No.: US 6,329,353 B1
(45) Date of Patent: Dec. 11, 2001

(54) CLEAR PERSONAL CARE FORMULATIONS CONTAINING QUATERNARY AMMONIUM COMPOUNDS AND OTHER NITROGEN-CONTAINING COMPOUNDS

(75) Inventors: Damon M. Dalrymple, Columbus, OH (US); Monna Manning, Columbus, OH (US); Frank Merz, Steinau (DE)

(73) Assignee: Goldschmidt Chemical Corporation, Hopewell, VA (US)

( * ) Notice: Subject to any disclaimer, the term of this patent is extended or adjusted under 35 U.S.C. 154(b) by 0 days.

(21) Appl. No.: 09/438,694

(22) Filed: Nov. 11, 1999

Related U.S. Application Data (63) Continuation-in-part of application No. PCT/US99/10405, filed on May 12, 1999.

(51) Int. Cl.[7] .................... A61K 31/685; A61K 31/16; A61K 31/155
(52) U.S. Cl. .................... 514/77; 514/613; 514/634
(58) Field of Search .................... 514/77, 613, 634

(56) References Cited

U.S. PATENT DOCUMENTS

| | | | |
|---|---|---|---|
| 5,439,682 | * | 8/1995 | Wivell et al. .................... 424/401 |
| 5,560,918 | * | 10/1996 | Wivell et al. .................... 424/401 |

FOREIGN PATENT DOCUMENTS

| | | |
|---|---|---|
| 10-81900 A | 11/1997 | (JP) . |
| 9-302382 A | 3/1998 | (JP) . |
| WO 97/03648 A | 2/1997 | (WO) . |
| WO 97/12020 | 4/1997 | (WO) . |

* cited by examiner

*Primary Examiner*—Kevin E. Weddington
(74) *Attorney, Agent, or Firm*—Scully, Scott, Murphy & Presser (57) ABSTRACT

A composition formulated from a primary anionic surfactant; optionally a secondary surfactant and/or a resin; and a nitrogen-containing compound of the structural formula:

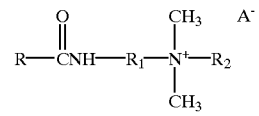

wherein R is a saturated, linear, branched or cyclic alkyl or aryl group containing 12 to 22 carbon atoms, with the proviso that R contains at least 80% of a single chain length and R is not lanolin, wheat germ or other natural broad-based chain distribution oil, $R_1$ is a saturated or unsaturated, linear, branched or cyclic alkyl or aryl group containing 1 to 6 carbon atoms and may contain one or more hydroxyl groups, $R_2$ is selected from the group consisting of hydrogen, methyl, ethyl and benzyl; and $A^-$ is a monovalent anion.

27 Claims, 5 Drawing Sheets

CLEAR PERSONAL CARE FORMULATIONS CONTAINING QUATERNARY AMMONIUM COMPOUNDS AND OTHER NITROGEN-CONTAINING COMPOUNDS

RELATED APPLICATIONS

This application is a continuation-in-part (CIP) application of PCT/US99/10405, filed May 12, 1999.

FIELD OF THE INVENTION

The present invention relates to formulations containing selected quaternary ammonium compounds that are useful for commercial products, for instance, personal care products such as hair conditioners, shampoos, skin conditioners, and the like. More particularly, the present invention relates to the use of selected quaternary ammonium compounds to make clear and thick formulations attractive and useful for commercial products.

BACKGROUND OF THE INVENTION

Although a variety of quaternary ammonium compounds or "quats" have been used and proposed for use in personal care products, many prior art quats have drawbacks associated therewith. For example, light color and low odor are essential for obtaining customer acceptance and for achieving stable and acceptable long-term product aesthetic properties. Indeed, there is increasing interest in obtaining personal care product formulations which are translucent or transparent (that is, clear) liquids, even to the point of obtaining a crystal clear dispersion. The discovery of such clear compositions requires careful identification of proper quaternary and/or polyquaternary ammonium compounds, together with appropriate additives, such as surfactants and solvents, which act together to achieve the desired appearance. Such clear personal care products would include: hair conditioners, shampoos, skin conditioners, body washes, liquid bath soaps, facial cleansers, make-up removers, baby baths, and hand soaps.

Each of these applications presents its own complications; because the interactions between the various components of the compositions must be considered in addition to the individual chemistry of each component. For example, consider the formulation of a combined conditioner and shampoo composition, also known as conditioning shampoos, two-in-one shampoos, or two-in-ones. Two-in-ones contain ingredients that both clean and condition the hair in one application and are thus very time efficient. Two-in-ones, however, are traditionally pearlescent or opaque because most conditioning ingredients, for example, quaternary ammonium compounds, are not soluble in anionic detergent carriers in the normal formulation parameters for these products. The detergent compounds with the widest range of cleaning properties are generally anionic (negatively charged) surfactants. Such anionic surfactants, for example, may include the alkylbenzene sulfonates, α-olefin sulfonates, sodium lauryl ether sulfates, sodium lauryl sulfates, ammonium lauryl ether sulfates, and ammonium lauryl sulfates available from Witco Corporation under the WITCOLATE® and WITCONATE® trademarks. In contrast, as exemplified by the quaternary ammonium compounds discussed above, conditioners are generally cationic (positively charged). Thus, when the anionic detergent ingredients and cationic conditioning ingredients are present in the same aqueous solution, as in two-in-ones, these ingredients have a natural tendency to complex together or even precipitate out of solution. This complexation or dispersion usually results in a pearlescent or opaque mixture which may interfere with the performance of both the detergent compound and conditioning compound and is therefore undesirable.

Moreover, it has been heretofore difficult to solubilize resins, e.g. anionic resins, in such prior art hair care formulations. Such resins typically require heat to ring open and reveal the anionic charge. Furthermore, it is extremely difficult to formulate these types of resins with cationic surfactants at all, let alone obtain clear formulations using these resins.

UK Patent No. 2 160 421 relates to a conditioning and softening composition that includes certain quaternary ammonium compounds. All of the examples prepared by this reference include coconut diethanolamide; a well-known thickening agent or viscosity-enhancing agent. The instant invention does not require diethanolamide or other conventional thickening agents or viscosity control agents, since the instant invention provides a clear formulation with a high viscosity from the components specified.

EP 0 511 652 A1 relates to a hair shampoo-conditioner formulation including an anionic cleansing surfactant, a polymeric cationic conditioning compound, a cationic conditioning surfactant, a fatty ester, and water. In contrast to the formulations of the instant invention, which are clear and have high viscosities, the compositions of EP 0 511 652 A1 are all opaque to pearlescent formulations (Examples 1 and 3–10), often with low viscosities. In addition, the compositions of EP 0 511 652 A1 require a polymeric cationic conditioning compound, such as quarternized guar gum, which is a conventional thickening agent that is not a required aspect of the instant invention, and is preferably excluded from the instant invention.

WO 97/12020 relates to a liquid laundry detergent formulation comprising an anionic surfactant component and a quaternary ammonium compound component. The compositions of WO 97/12020 are not said to be clear or exhibit high viscosity and, as set forth in more detail below, formulations made according to the teachings of the Examples of WO 97/12020 are not clear.

In some prior art formulations, lanolin, wheat germ and other natural broad-based chain distribution oils are used as the quaternary ammonium compound. The use of such quaternaries is not advantageous since the same do not build-up viscosity; therefore those quaternaries cannot achieve the benefits of the present invention.

SUMMARY OF THE INVENTION

The present invention is directed to novel formulations that are particularly useful for personal care products which include, for example, hair conditioners, shampoos, two-in-one shampoo/conditioners, skin conditioners, body washes, liquid bath soaps, facial cleansers, make-up removers, baby baths, and hand soaps. The formulations of the present invention are clear and may be made thick, both of which are highly desirable and attractive properties for personal care products. Thus, the formulations of the present invention overcome the problems in the art discussed above, and also exhibit the properties and advantages described herein.

One aspect of the present invention comprises a clear composition formulated from ingredients comprising:

(a) a primary anionic surfactant;
(b) optionally a secondary surfactant and/or a resin; and
(c) a nitrogen-containing compound of structural formula (1):

(1)

wherein
R is a saturated or unsaturated, linear, branched or cyclic alkyl or aryl group containing 12 to 22 carbon atoms that is unsubstituted;
$R_1$ is a saturated or unsaturated, linear, branched or cyclic alkylene group containing 1 to 6 carbon atoms and 0 to 3 hydroxyl groups;
$R_2$ is selected from the group consisting of hydrogen, methyl, ethyl, and benzyl; and
$A^-$ is a monovalent anion.

In the present invention, at least about 80%, and most preferably about 90%, of the total amount of the nitrogen-containing compounds comprises nitrogen-containing compounds having a common R group (that is, of the same chain length or, more preferably of the same group). Moreover, nitrogen compounds of formula (1) wherein R is equal to lanolin, wheat germ or other broad-based chain distribution oils, i.e. whole oils, are excluded from the present invention. These whole oils are excluded because they cannot build-up viscosity; therefore those quats cannot achieve the benefits mentioned herein.

In embodiments wherein the formulation is a two component system (binary system) comprising a primary anionic surfactant and a nitrogen-containing compound of formula (1), the weight ratio of the primary anionic surfactant to the nitrogen-containing compound is from 12:1 to 1:12, with a weight ratio of the primary anionic surfactant to nitrogen-containing compound of from 8:1 to 1:8 being highly preferred.

In another preferred embodiment of the present invention, the formulation is a ternary system including the secondary surfactant or the resin as an additional essential component. In embodiments wherein a ternary formulation comprising a primary anionic surfactant, a secondary surfactant and a nitrogen-containing compound of formula (1) is employed, the weight ratio of secondary surfactant to nitrogen-containing compound is from 6:1 to 1:6, with a weight ratio from 3:1 to 1:3 being more preferred. In another embodiment, the formulation is a binary system comprising a secondary surfactant and the quaternary ammonium compound of formula (1). In this embodiment, the weight ratio of secondary surfactant to nitrogen-containing compound is from 12:1 to 1:12, with a weight ratio of 8:1 to 1:8 being highly preferred.

As used herein, the term "unsubstituted" means that the group does not contain any atoms other than carbon and hydrogen within the group.

As used herein, the term "primary anionic surfactant" is intended to include any anionic surfactant, such as ammonium lauryl sulfate, sodium lauryl sulfate, any α-olefin sulfonate, ammonium laureth sulfate (2 or 3 moles EO), sodium laureth sulfate(2 or 3 moles EO), sodium myristyl sulfate, sodium myristeth sulfate (1–4 moles EO), TEA-dodecylbenzene sulfonate (TEA denotes triethanolamine), TEA lauryl sulfate, ammonium pareth sulfate, sodium pareth sulfate, sodium oleth sulfate, linear alkyl benzene sulfonate (LAS), derivatives of any of the forgoing, and similar compounds known to those of skill in the art, and mixtures thereof.

As used herein, the term "secondary surfactant" is intended to include amphoteric surfactants, non-ionic surfactants, betaines, sulfosuccinates, mono- and diglycerides, glycinates, sugars and derivatives thereof, hydroxysultaines, mono- and diacetates, ethoxylated derivatives of any of the forgoing, and similar compounds known to those of skill in the art, and mixtures thereof. The purpose of the secondary surfactant, which represents an optional ingredient of the present invention, is to enhance the charge interaction in such a way that no precipitation occurs. Any surfactant that accomplishes or would be expected to accomplish this result may be used as the optional secondary surfactant in the present invention. Although not limited to the following, the hydrophobic moieties of the optional secondary surfactant may be derived from any of the following whole oils or mixtures thereof: tallow, jojoba, palm, coconut, avocado, babassu, wheat germ, rapeseed, olive, orange, corn, linseed, neem, peanut, safflower, sesame seed, soybean, sunflower seed, and cocoa butter.

The term "resin" is used herein to denote any polymeric anionic resin, particularly a maleic acid-containing copolymer with anionic charges, such as those sold under the tradename GANTREZ and OMNIREZ by ISP, and similar resins. As stated in the background section of this application, such resins typically require heat to ring open and reveal the anionic charge. Thus, a heating step to an appropriate temperature during mixing of the ingredients is important. The formulations of the present invention, which contain a resin as one of the essential ingredients, however, are proven to be compatible with anionic polymeric resins without precipitation or clouding, and give a clear formulation. Moreover, the order of addition of the various components of the formulations are not important and even precipitated resin can be resolubilized in formulations according to the present invention.

Another aspect of the invention eliminates the primary anionic surfactant. In this embodiment of the present invention, the inventive formulation comprises the nitrogen-containing compound of formula (I) and the optional secondary surfactant and/or the resin as essential components. The weight ratio of secondary surfactant to nitrogen-containing compound in this embodiment is from 12:1 to 1:12, with a weight ratio of 8:1 to 1:8 being preferred.

Yet another aspect of the present invention comprises a composition formulated from ingredients comprising:
(a) a primary anionic surfactant;
(b) optionally a secondary surfactant and/or resin; and
(c) a nitrogen-containing compound of the structural formula (2):

(2)

wherein
R is a saturated or unsaturated, linear, branched or cyclic alkyl or aryl group containing 12 to 22 carbon atoms that is unsubstituted; and
$A^-$ is a monovalent anion, with the proviso that R contains at least 80% or more of a single chain length (or species) and R is not a whole oil.

In a preferred embodiment of the present invention, the primary anionic surfactant is selected from the group consisting of ammonium lauryl sulfate, sodium lauryl sulfate, an α-olefin sulfonate, ammonium laureth sulfate (2 or 3 moles EO), sodium laureth sulfate (2 or 3 moles EO), sodium myristyl sulfate, sodium myristeth sulfate (1–4 moles EO), TEA-dodecylbenzene sulfonate, TEA lauryl sulfate, ammonium pareth sulfate, sodium pareth sulfate, sodium oleth sulfate, linear alkyl benzene sulfonate (LAS), derivatives of any of the forgoing, and mixtures thereof.

In another preferred embodiment of the present invention, the primary anionic surfactant comprises between about 1 wt. % to about 50 wt. % (expressed as actives) of the total amount of components (a), optional (b), and (c), expressed as actives. In yet another preferred embodiment of the present invention, the primary anionic surfactant (as actives) comprises between about 2 wt. % to about 25 wt. % (expressed as actives) of the total amount of components (a), optional (b), and (c), expressed as actives. In a further preferred embodiment of the present invention, the primary anionic surfactant (as actives) comprises between about 5 wt. % to about 15 wt. % (expressed as actives) of the total amount of components (a), optional (b), and (c), expressed as actives.

In embodiments wherein a resin is employed, the resin component comprises between about 0.01 wt. % to about 3.0 wt. %, more preferably between about 0.025 wt. % to about 1.5 wt. %, and even more preferably between about 0.50 wt. % to about 0.75 wt. % of the total amount of components (a), (b) and (c) expressed as actives.

In another preferred embodiment of the present invention, the secondary surfactant, which represents an optional ingredient of the present invention, is selected from the group consisting of cocamidopropyl betaine, lauramidopropyl betaine, ricinoleamidopropyl betaine, myristamidoproyl betaine, palmamidopropyl betaine, stearamidopropyl betaine, behenamidopropyl betaine, erucamidopropyl betaine, cocamidopropyl hydroxysultaine, myristamidopropyl hydroxysultaine, palmamidopropyl hydroxysultaine, stearamidopropyl hydroxysultaine, behenamidopropyl hydroxysultaine, erucamidopropyl hydroxysultaine, disodium lauroamphodiacetate, disodium cocamphodiacetate, disodium myristamphodiacetate, disodium palmamphodiacetate, disodium stearamphodiacetate, disodium behenamphodiacete, disodium erucamphodiacetate, sodium lauryl amphoacetate, sodium cocamphoacetate, sodium cocoamphopropionate, sodium laurylamphopropionate, disodium lauroamphodipropionate, sodium lauryl sulfosuccinate, disodium laureth sulfosuccinate, cocobetaine, laurylbetaine, myristylbetaine, stearylbetaine, behenylbetaine, PEG 1-300 glyceryl cocoate, such as PEG 200 glyceryl cocoate, PEG 1-300 glyceryl tallowate, PEG 1-500 hydrogenated glyceryl palmitate, coco-glucoside, lauryl glucoside, decyl glucoside, sodium xylene sulfonate, and mixtures thereof.

In another preferred embodiment of the present invention, the optional secondary surfactant comprises between about 0.1 wt. % to about 50 wt. % (expressed as actives) of the total amount of components (a), (b), and (c), expressed as actives. In yet another preferred embodiment of the present invention, the optional secondary surfactant comprises between about 0.5 wt. % to about 10 wt. % (expressed as actives) of the total amount of components (a), (b), and (c), expressed as actives. In a further preferred embodiment of the present invention, the optional secondary surfactant comprises between about 2 wt. % to about 8 wt. % (expressed as actives) of the total amount of components (a), (b), and (c), expressed as actives.

In yet another preferred embodiment of the present invention, the nitrogen-containing compound (which may be of formula (1) and/or (2)) comprises between about 0.1 wt. % to about 50 wt. % (expressed as actives) of the total amount of components (a), optional (b), and (c), expressed as actives. In yet another preferred embodiment of the present invention, the nitrogen-containing compound comprises between about 0.5 wt. % to about 20 wt. % (expressed as actives) of the total amount of components (a), optional (b), and (c), expressed as actives. In a further preferred embodiment of the present invention, the nitrogen-containing compound comprises between about 0.75 wt. % to about 10 wt. % (expressed as actives) of the total amount of components (a), optional (b), and (c), expressed as actives.

Examples of the nitrogen-containing compounds according to the instant invention include: palmitamidopropyltrimonium chloride, behenamidopropyl trimonium chloride, cetylamidopropyltrimonium chloride, palmitamidopropyltrimonium bromide, and stearylamidopropyl methosulfate. It is again emphasized that the nitrogen-containing compounds of the present invention are not based on whole oils; instead they are (derived) refined from fatty acids.

In a preferred embodiment of the invention, the composition further comprises a salt, the salt may be selected from the group consisting of sodium chloride, potassium chloride, calcium chloride, magnesium chloride, ammonium chloride, sodium bromide, potassium bromide, calcium bromide, magnesium bromide, ammonium bromide, sodium iodide, potassium iodide, calcium iodide, magnesium iodide, ammonium iodide, sodium acetate, potassium acetate and mixtures thereof. The salt component, if present, may be used to modify the viscosity of the resulting composition. In a further preferred embodiment of the present invention, the salt component comprises between about 0.2 wt. % to about 50 wt. %, more preferably between about 0.4 wt. % to about 5 wt. %, and most preferably between about 0.5 wt. % to about 3 wt. % of the total amount of components (a), optional (b), and (c), expressed as actives. In some embodiments of the invention, the composition does not contain a significant amount of any salts.

In certain embodiments of the present invention, the composition does not contain a significant amount of any conventional thickening agents. Indeed, conventional thickening agents which would hinder the clarity of the final product such as fatty acids, pearlescent agents and certain alkyl amides are excluded from the present invention. The term "conventional thickening agents" as used herein means any thickening agent or viscosity-enhancing agent known to those of skill in the art, excepting salts. Examples of such conventional thickening agents include: quaternized guar gum, hydroxypropyl-substituted guar gum (such as that available from Rhône-Poulenc Corporation under the tradename JAGUAR® HP200), polyethylene glycol (such as that available from Union Carbide Corporation under the tradename CARBOWAX® 20M), hydrophobic modified hydroxyethylcellulose (such as that available from the Aqualon Company under the tradename NATROSOL® Plus), organophilic clays and alkyl amides such as cocamide DEA.

DETAILED DESCRIPTION OF THE INVENTION

The present invention is directed to novel formulations that are particularly useful for personal care products which include, for example, hair conditioners, shampoos, two-in-one shampoo/conditioners, skin conditioners, body washes, liquid bath soaps, facial cleansers, make-up removers, baby baths, and hand soaps. The formulations of the present invention are clear and also show unexpected viscosity building properties and may be made thick, both highly desirable and attractive properties for personal care products. The hair conditioner and two-in-one shampoo/conditioner formulations of the present invention exhibit good static decay reduction of the hair tress and exceptional conditioning feel.

Examples and experiments were conducted to illustrate the present invention. These examples are intended only to be illustrative of the present invention and are not intended to limit the present invention. The wt. % of ingredients shown in the Examples below is the amount of the ingredient weighed out as obtained and added to the formulation; in order to determine the amount of each active ingredient, that is, the wt. % of that component expressed as actives ("wt. % (as actives)"), use the percentage of the actives of that component and multiply by the wt. % given. For example, when sodium laureth sulfate (2 moles EO) (26% actives) is specified as 50.0 wt. % of the formulation, only (50.0×0.26) or 13 wt. % (as actives) of sodium laureth sulfate is present in the formulation. Although not indicated therein, each of the formulations (Formulations A–H and J–K) may have a resin component according to the present invention incorporated and/or solubilized therein. Such resin-containing formulations would be clear and would form one phase or a gel. It is also within the contemplation of the present invention to substitute a resin in place of the secondary surfactants in Formulations A–H and J–K. Such formulations would also be clear and exhibit the properties mentioned herein.

EXAMPLES

Formulations A–E were prepared by measuring the individual ingredients into a vessel and mixing the resulting mixture at room temperature until it turned clear. The $C_{16}$ DMAPA-based quat in Formulations A–E is palmitamidopropyltrimonium chloride. As used herein, the prefix attached to the DMAPA-based quat, for example, $C_{16}$ or $C_{12}$, designating the average number of carbon atoms in the R group of formula (1) and (2). Note that the "$C_{16}$" designation is not meant to imply that all of the chain lengths are $C_{16}$, as commercial grade fatty acids derived from natural sources are a mixture of various chain lengths; "$C_{16}$" is therefore meant to indicate the average chain length of the R group. As noted below, the pH of the resulting formulations may be adjusted by the addition of, for example, sodium hydroxide or citric acid. Perfumes, preservatives, dyes and other additives may also be added, and the amount of sodium chloride can be varied to adjust the viscosity. The term "actives", is well-known to those of skill in the art, and denotes the amount of actual substance of interest in a given carrier, such as water or propylene glycol, and is usually expressed in percent. Thus, adding 1 gram of $C_{16}$ DMAPA-based quat solution (30% actives) contributes 0.3 grams of $C_{16}$ DMAPA-based quat to the formulation.

| Ingredient | Wt. % |
|---|---|
| FORMULATION A | |
| Sodium laureth sulfate (2 mole EO) (26% actives) | 13.0 |
| $C_{16}$ DMAPA-based quat (30% actives) | 1.8 |
| PEG-200 hydrogenated glyceryl palmate/PEG-7 glyceryl cocoate (70% actives) | 1.5 |
| Sodium chloride | 1.0 |
| Deionized water | qs to 100 |
| FORMULATION B | |
| Sodium laureth sulfate (2 mole EO) (26% actives) | 38.46 |
| $C_{16}$ DMAPA-based quat (30% actives) | 16.67 |
| Cocamidopropyl betaine (35% actives) | 14.29 |
| Deionized water | qs to 100 |
| FORMULATION C | |
| Sodium laureth sulfate (2 mole EO) (26% actives) | 50.0 |
| $C_{16}$ DMAPA-based quat (30% actives) | 6.6 |
| Cocamidopropyl betaine (35% actives) | 5.1 |
| Sodium chloride | 1.0 |
| Deionized water | qs to 100 |
| FORMULATION D | |
| Sodium laureth sulfate (2 mole EO) (26% actives) | 50.0 |
| $C_{16}$ DMAPA-based quat (30% actives) | 6.6 |
| Cocamidopropyl hydroxysultaine (48% actives) | 3.75 |
| Sodium chloride | 1.0 |
| Deonized water | qs to 100 |
| FORMULATION E | |
| α-Olefin sulfonate (39% actives) | 33.3 |
| $C_{16}$ DMAPA-based quat (30% actives) | 6.6 |
| Cocamidopropyl betaine (35% actives) | 5.1 |
| Sodium chloride | 1.0 |
| Deionized water | qs to 100 |

Formulations A–E demonstrate that various combinations of a $C_{16}$ DMAPA-based quat, specifically, palmitamidopropyltrimonium chloride, with sulfates or sulfonates in combination with betaines, hydroxysultaines, or ethoxylated mono- and diglycerides, produce clear systems whose viscosity may be readily adjusted.

Comparative Formulations X and Y below were made using the same procedure used in making Formulations A–E.

| Ingredient | Wt. % |
|---|---|
| COMPARATIVE FORMULATION X | |
| Sodium laureth sulfate (2 mole EO) (26% actives) | 50.0 |
| Cetyl trimethyl ammonium chloride (CTAC) (25% actives) | 8.0 |
| Cocamidopropyl betaine (35% actives) | 5.1 |
| Sodium chloride | 1.0 |
| Deionized water | qs to 100 |
| COMPARATIVE FORMULATION Y | |
| Sodium laureth sulfate (2 mole EO) (26% actives) | 50.0 |
| $C_{16}$ DMAPA-based quat (30% actives) | 6.6 |
| Cocamidopropyl betaine (35% actives) | 5.1 |
| Sodium chloride | 1.0 |
| Deionized water | qs to 100 |

Comparative Formulation X did not become clear or thick with the addition of sodium chloride and demonstrates that a DMAPA-based quat is a critical component in a formulation possessing such properties.

Comparative Formulation Y, as made, was initially clear with up to 5% actives of the $C_{16}$ DMAPA-based quat. When an additional 1% actives of the $C_{16}$ DMAPA-based quat (3.33 grams) was added, the solution became cloudy and then clear. When a further 1% actives of the $C_{16}$ DMAPA-based quat (3.33 grams) was added to the solution, however, the solution remained cloudy. This demonstrates that there is a unique relationship between the ratio of primary anionic surfactant to secondary surfactant to DMAPA-based quat in making a clear formulation.

Formulations F–K were made to demonstrate that these clear formulations could be made with other chain lengths of DMAPA-based quats. Three DMAPA-based quats were synthesized with various alkyl chain lengths: (1) a $C_{12}$ DMAPA chloride quat in water (30.56% quat actives uncorrected; liquid state); (2) a $C_{22}$ DMAPA chloride quat in a propylene glycol solvent system (47.36% quat actives uncorrected; nonviscous liquid state); and (3) a $C_{18}$ DMAPA dimethyl sulfate quat (80% quat actives uncorrected; solid state). All three quats were formulated into clear systems in combination with an anionic surfactant and an amphoteric surfactant or ethoxylated mono- or diglyceride. Viscosity measurements were also taken with control Formulation I, containing no quat, to show the thickening properties of the DMAPA-based quats.

| Ingredient | Wt. % |
|---|---|
| FORMULATION F | |
| Sodium laureth sulfate (2 mole EO) (26% actives) | 48.1 |
| $C_{18}$ DMAPA-based DMS quat (80% actives) | 2.5 |
| Cocamidopropylbetaine (35% actives) | 5.1 |
| Deionized water | 43.3 |
| Sodium chloride | 1.0 |

All ingredients were combined at room temperature, the blend was heated until the quat dissolved and the formulation was even. Formulation F is clear.

| Ingredient | Wt. % |
|---|---|
| FORMULATION G | |
| Sodium laureth sulfate (2 mole EO) (26% actives) | 48.1 |
| $C_{22}$ DMAPA-based quat in propylene glycol (47.36% actives) | 4.2 |
| Cocamidopropylbetaine (35% actives) | 5.1 |
| Deionized water | 41.6 |
| Sodium chloride | 1.0 |

All ingredients were combined at room temperature and mixed until even. Formulation G was slightly hazy initially, but then went clear.

| Ingredient | Wt. % |
|---|---|
| FORMULATION H | |
| Sodium laureth sulfate (2 mole EO) (26% actives) | 48.1 |
| $C_{12}$ DMAPA-based DMS quat (30.56% actives) | 6.5 |
| Cocamidopropylbetaine (35% actives) | 5.1 |
| Deionized water | 39.3 |
| Sodium chloride | 1.0 |

All ingredients were combined at room temperature and mixed until even. Formulation H was slightly hazy initially, but then went clear.

| Ingredient | Wt. % |
|---|---|
| FORMULATION I | |
| Sodium laureth sulfate (2 mole EO) (26% actives) | 48.1 |
| Cocamidopropyl betaine (36% actives) | 5.1 |
| Deionized water | 45.8 |
| Sodium chloride | 1.0 |

Formulation I was made as a control formulation. All ingredients were combined at room temperature, mixed until even and the resulting formulation was clear. The viscosity of the above formulations were measured with a Brookfield DV2 RVT viscometer (available from Brookfield Engineering Laboratories, Inc.), Spindle #6, 10 rpm, 25° C. and the results are shown in Table 1.

TABLE 1

| Formulation | Viscosity (cps) |
|---|---|
| Formulation F ($C_{18}$ DMAPA-based quat formulation) | 19,000 |
| Formulation G ($C_{22}$ DMAPA-based quat formulation | 22,100 |
| Formulation H ($C_{12}$ DMAPA-based quat formulation) | 38,300 |
| Formulation I (control formulation) | 300 |

The result presented in Table 1 is surprising, as the formulation based on DMAPA-quats having a shorter chain length (Formulation H) has a higher viscosity than the formulation based on DMAPA-quats having a longer chain length (e.g., Formulation G). It has been determined that the viscosity of a particular formulation according to the instant invention is enhanced by using the nitrogen-containing compounds of formula (1) where the R groups have the same chain length or consist of the same groups. Thus, if a particular formulation according to the invention contains nitrogen containing compounds, the viscosity will increase as the chain length distribution decreases.

Formulations containing only the primary anionic surfactant (in this case, SLES-2) and $C_{12}$, $C_{16}$, and $C_{22}$ nitrogen-containing compounds of formula (1) according to the present invention were also prepared. From these formulations it was found that such compositions of the present invention (a) provide significant viscosity without the addition of salt or conventional thickening agent; (b) exhibit a rapid and significant increase in viscosity with the addition of salt; (c) maintain such high viscosity at elevated temperatures; (d) exhibit an increase in viscosity with increase temperature (from 20° C. to 30° C.).

A similar formulation using a quat outside the scope of the claimed invention (such as that sold by Witco Surfactant GmbH under the tradename REWOQUAT® RTM50) does not display any of these characteristics. Moreover, the composition according to the present invention mitigated the skin-irritating effects of the primary anionic surfactant and nitrogen-containing compounds of formula (1) in the formulation, which was particularly marked with the weight ratio of the primary anionic surfactant to the nitrogen-containing compounds of formula (1) was between about 3:1 to about 1:3; preferably between about 2:1 to about 1:2; more preferably between about 5:3 to about 3:5; and most preferably between about 3:2 to about 2:3. This seems to indicate that a complex is formed between these two components and the effects are expected to be present in the formulations according to the instant invention that also contain a secondary surfactant.

Additional formulations J and K were made to show that the various alkyl chain lengths of the DMAPA-based quats could form clear systems in mono/diglycerides and diacetates.

| Ingredient | Wt. % |
|---|---|
| FORMULATION J | |
| Sodium laureth sulfate (2 mole EO) (26% actives) | 22.2 |
| $C_{22}$ DMAPA-based quat in propylene glycol (47.36% actives) | 6.3 |
| Disodium cocoamphodiacetate (50% actives) | 10.0 |
| Deionized water | 61.5 |

All ingredients were combined at room temperature and mixed until even. Formulation J was slightly hazy initially, but then went clear and is a gel.

| Ingredient | Wt. % |
|---|---|
| FORMULATION K | |
| Sodium laureth sulfate (2 mole EO) (26% actives) | 22.2 |
| $C_{12}$ DMAPA-based quat in water (30.56% actives) | 9.82 |
| PEG-200 hydrogenated glyceryl palmate/PEG-7 glyceryl cocoate (70% actives) | 10.0 |
| Deionized water | 60.84 |

All ingredients were combined at room temperature and mixed until even. Formulation K was slightly hazy initially, but then went clear and is slightly viscous.

Example Formulation According to WO 97/12020

In order to test the performance of the compositions of the instant invention over the formulations prepared in WO 97/12020, the formulation A of Example III in WO 97/12020 was attempted, substituting similar ingredients where the specified ingredients were not available or particularly set forth; however, the following ingredients specified for formulation A of Example III was not incorporated into the formulation because they could not be obtained, or it was unclear what they were: diethylenetriamine pentamethylene phosphonic acid (specified as 1.0 wt. %); Endo A (5000 CEVU/g) (specified as 0.05 wt. %); terephthalate based polymer (specified as 0.5 wt. %); and DC 3225C (specified as 0.04 wt. %); these unincorporated ingredients account for less than 2% of the formulation and they would not be expected to affect the clarity or opaqueness of the final product.

| | COMPARATIVE FORMULATION WO 97/12020 | | |
|---|---|---|---|
| Blend | Ingredient used [ingredient specified in WO 97/12020 (if different from that used)] | Wt. % | Amount used (g) |
| A | SLES-3 (Witcolate ES-3) [$C_{12-15}$ alkyl ethoxylated sulfate] | 2.0 | 6.0 |
| A | SLS (Witcolate WAC LA) [$C_{12-15}$ alkyl sulfate] | 17.0 | 51.0 |
| A | Citric Acid Anhydrous | 1.0 | 3.0 |
| A | Ethanol | 1.8 | 5.4 |
| A | Boric Acid | 2.4 | 7.2 |
| A | DI Water | 26.16 | 78.48 |
| B | VARISOFT ® PATC [palmitamidopropyltrimonium chloride] | 2.0 | 6.0 |
| B | $C_{12-14}$ N-methyl glucamide | 5.0 | 15.0 |
| B | Alfonic 1214 EO 4.7 [$C_{12-14}$ fatty alcohol ethoxylate] | 6.0 | 18.0 |
| B | Industrene 7018 [$C_{12-18}$ fatty acid] | 11.0 | 33.0 |
| B | Nonoethanolamine (98%) | 8.8 | 24.0 |

-continued

COMPARATIVE FORMULATION WO 97/12020

| Blend | Ingredient used [ingredient specified in WO 97/12020 (if different from that used)] | Wt. % | Amount used (g) |
|---|---|---|---|
| B | Sodium Hydroxide | 1.0 | 3.0 |
| B | Propanediol | 14.5 | 43.5 |
| B | 2-Butyl-1-octanol [2-Butyl Octanol] | 1.0 | 3.0 |
|  | UCT polydimethylsiloxane: T-structure branch terminus PS-410KG [Branched Silicone] | 0.3 | 0.9 |
| C | Termanyl 300 LDX [Amylase 300 KNU/g] | 0.1 | 0.3 |
| C | Lipolase 100L [Lipase D96/L 100 KNU/g] | 0.15 | 0.45 |
| C | Savinase 16.0 L-type EX [Protease 35 g/L] | 0.5 | 1.5 |
| C | Carenzyme 4500G [Carenzyme 5000 CEVU/g] | 0.09 | 0.27 |

Blend A ingredients were combined in a vessel and heated over a steam bath to approximately 80° C. Blend B ingredients were combined in a separate vessel to form Blend A+B. The first time this Blend A+B cooled down, the glucamide separated from the rest of the blend. The Blend A+B was reheated in a water bath to approximately 80° C. and stirred with cooling. Blend C was added when the Blend A+B reached room temperature to form Blend A+B+C. The resulting Blend A+B+C (a formulation according to the teachings of WO 97/12020) is a creamy, opaque emulsion which was not clear. This is probably primarily due to the significant proportion of fatty alcohol ethoxylate and fatty acid, where the former acts as an emulsifying agent and the latter which, along with other ingredients found in the formulation, acts as an opacifying agent and thickener.

Ternary Phase Diagrams

Figure 1:
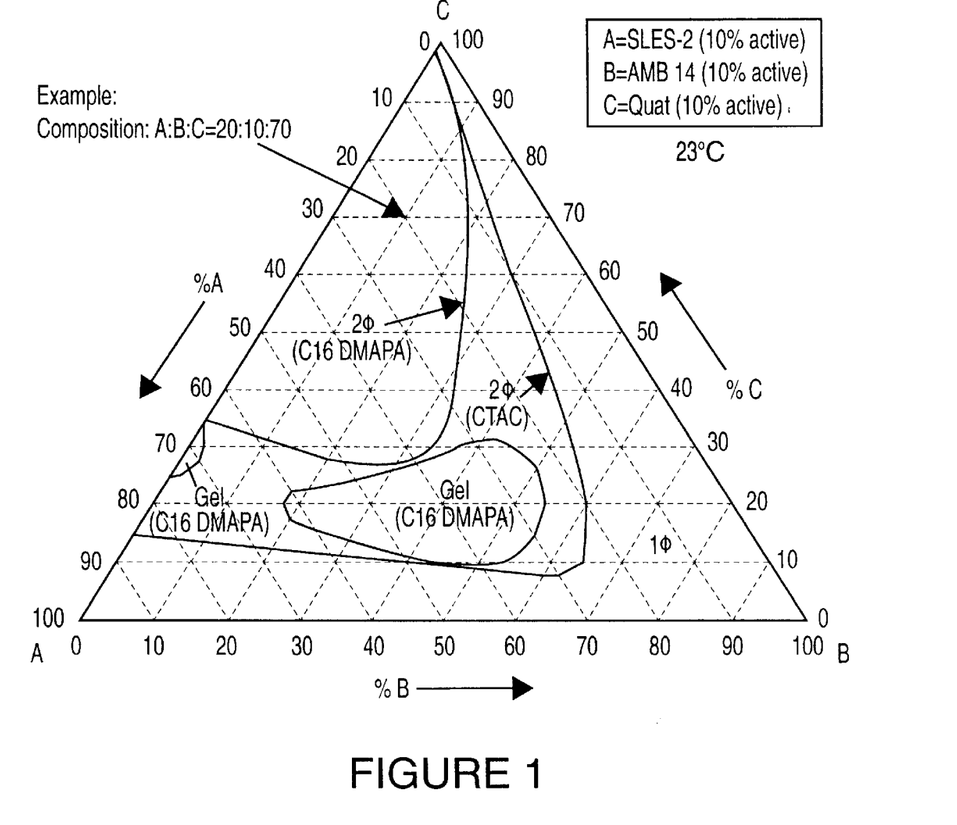
FIG. 1 is a phase diagram illustrating the contrast between two ternary systems having components A, B, and C, wherein component A is sodium laureth sulfate (SLES-2), component B is cocamidopropyl betaine (AMB 14), and component C is either a dimethyl amidopropyl amine-based (DMAPA-based) quat or cetyl trimethyl ammonium chloride (CTAC).
Figure 2:
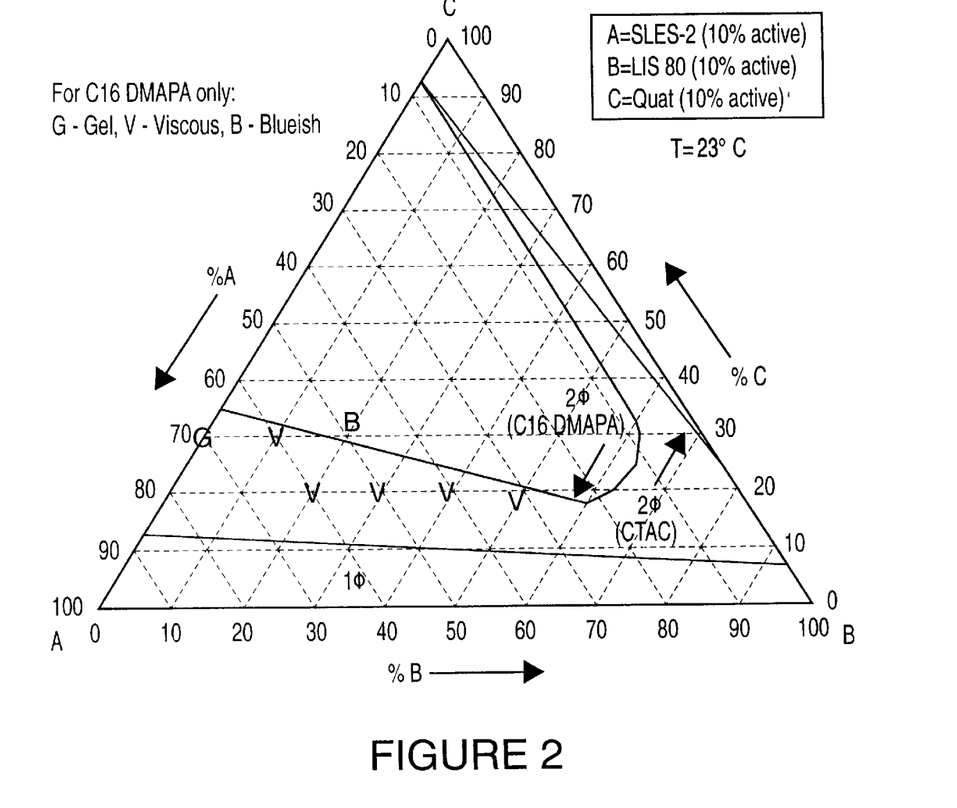
FIG. 2 is a phase diagram illustrating the contrast between two ternary systems having components A, B, and C, wherein component A is sodium laureth sulfate (SLES-2), component B is PEG-200 hydrogenated glyceryl palmate/ PEG-7 glyceryl cocoate (LI S 80), and component C is either a DMAPA-based quat or CTAC.
Figure 3:
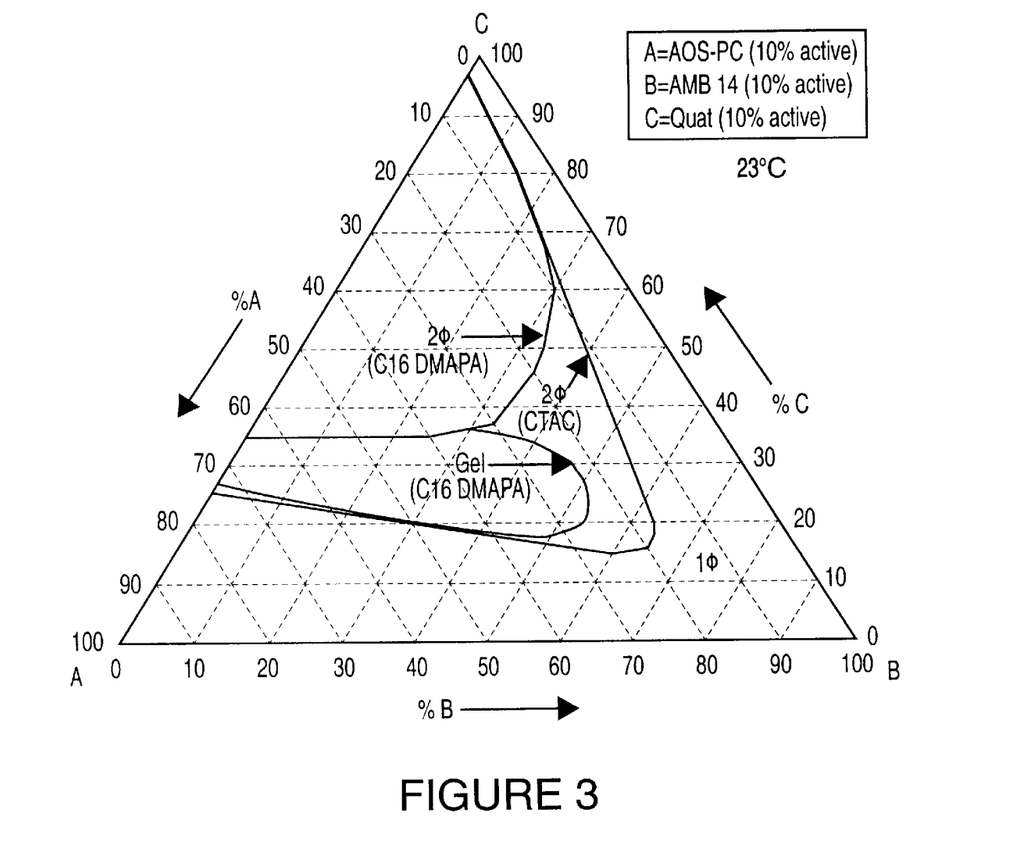
FIG. 3 is a phase diagram illustrating the contrast between two ternary systems having components A, B, and C, wherein component A is $C_{14-16}$ α-olefin sulfonate (AOS-PC), component B is cocamidopropyl betaine (AMB 14), and component C is either a DMAPA-based quat or CTAC.

Six ternary phase diagrams were prepared at 23° C. to illustrate the difference in performance between a certain $C_{16}$ DMAPA-based quat (palmitamidopropyltrimonium chloride) and cetyl trimethyl ammonium chloride or cetrimonium chloride (CTAC) (available from Witco Corporation under the tradename VARISOFT® 300). These six ternary phase diagrams are presented in FIGS. 1 to 3, where each Figure contains two diagrams. Each Figure, therefore, contains data for two separate ternary diagrams or systems: components A and B, which are the same for the two systems in a particular Figure, and component C, which is either the $C_{16}$ DMAPA-based quat (in one system) or CTAC (in the other system). Thus, ternary systems 1 and 2 are illustrated in FIG. 1, ternary systems 3 and 4 are illustrated in FIG. 2, and ternary systems 5 and 6 are illustrated in FIG. 3. The three components of each these systems is set forth in Table 2.

TABLE 2

|  | FIG. 1 | | FIG. 2 | | FIG. 3 | |
|---|---|---|---|---|---|---|
| INCI Name (abbreviation) | 1 | 2 | 3 | 4 | 5 | 6 |
| Sodium laureth sulfate (SLES-2) | X | X | X | X |  |  |
| Cocamidopropyl betaine (AMB 14) | X | X |  |  | X | X |
| Trimethylamidopropyl ammonium chloride ($C_{16}$ DMAPA-based quat) | X |  | X |  | X |  |
| Cetyl trimethyl ammonium chloride (CTAC) |  | X |  | X |  | X |
| Sodium $C_{14-16}$ α-olefin sulfonate (AOS-PC) |  |  |  |  | X | X |

TABLE 2-continued

|  | FIG. 1 | | FIG. 2 | | FIG. 3 | |
|---|---|---|---|---|---|---|
| INCI Name (abbreviation) | 1 | 2 | 3 | 4 | 5 | 6 |
| PEG-200 hydrogenated glyceryl palmate/PEG-7 glyceryl cocoate (LI S 80) |  |  | X | X |  |  |

As is typical of ternary phase diagrams, each corner of the phase diagram represents one species only (10% actives); for example, at corner C, only the quaternary compound or quat (either 10% $C_{16}$ DMAPA-based quat or CTAC actives) is present. Moreover, there are boundary lines that indicate phase changes for each of the six ternary systems presented in FIGS. 1 to 3. The regions or composition ranges of a ternary system having a single phase are indicated by the symbol 1φ. The boundary line separating the region or composition range having one phase (1φ) and the region or composition range having two phases is indicated by an arrow having a legend with the symbol 2φ and indicating whether the boundary line applied to the DMAPA-based quat ternary system or the CTAC ternary system of that Figure. Additionally, any gel regions or compositions that exist for the ternary systems are labeled and it is indicated whether such gel regions apply to the DMAPA-based quat ternary system or the CTAC ternary system of that Figure.

In each of the experiments used to construct the ternary phase diagrams presented in FIGS. 1 to 3, a series of samples of 10 gram sample size were prepared in 20 mL vials. The anionic surfactants of the systems were always added last. Each sample was shaken by hand or, if necessary, by using a mechanical vibrator. Each sample was then put aside until the next day. The samples were then examined and the appearance of a phase boundary or gel phase or lack thereof was determined and such information was used to construct each ternary phase diagram. A sample was said to be two phase (2φ) if the sample showed a significantly bluish, turbid, or milky appearance.

It should be noted that the presence of gel or thickened phase regions in the $C_{16}$ DMAPA-based quat ternary phase diagram is desirable for formulating products such as shampoos and body washes because it allows the formulators the freedom to choose desired viscosity.

FIG. 1

As shown in Table 2, FIG. 1 contains ternary systems 1 and 2 which each have sodium laureth sulfate (SLES-2), available from Lonza, Inc. under the tradename CARSONOL® SLES-2, as component A, cocamidopropyl betaine (AMB 14), available from Witco Corporation under the tradename REWOTERIC® AMB 14, as component B, and either a $C_{16}$ DMAPA-based quat (ternary system 1) or CTAC (ternary system 2) as component C. In FIG. 1, the location of an example of a particular ternary composition (A:B:C=20:10:70), is indicated, including 20 wt % of SLES-2, 10 wt. % of AMB, and 70 wt. % of either the $C_{16}$ DMAPA-based quat (ternary system 1) or CTAC (ternary system 2). This particular composition indicated is in the two phase (2φ) region in both the $C_{16}$ DMAPA-based quat and the CTAC phase diagrams. Turning again to FIG. 1, it can be seen that the corresponding ternary phase system of the $C_{16}$ DMAPA-based quat is different from that of CTAC. As can be seen in FIG. 1, the introduction of the DMAPA unit into the quat molecule changes the interaction between the quat and the anionic surfactant and unexpectedly leads to a richer phase behavior. Some important aspects of the difference between the behavior of the $C_{16}$ DMAPA-based quat and CTAC discovered during these experiments and illustrated in FIG. 1 may be summarized as follows:
a. The $C_{16}$ DMAPA-based quat phase diagram has a much smaller two phase (2φ) region than that of the CTAC phase diagram.
b. The $C_{16}$ DMAPA-based quat phase diagram has two gel phase regions (each very viscous), while the CTAC phase diagram has none.
c. The $C_{16}$ DMAPA-based quat gel phases are clear.
d. The large two phase (2φ) region in the CTAC phase diagram contrasts with the two smaller gel phases and smaller two phase (2φ) region in the $C_{16}$ DMAPA-based quat phase diagram.

FIG. 2

As shown in Table 2, FIG. 2 contains ternary systems 3 and 4 which each have sodium laureth sulfate (SLES-2), available from Lonza, Inc. under the tradename CARSONOL® SLES-2, as component A, PEG-200 hydrogenated glyceryl palmate/PEG-7 glyceryl cocoate (LI S 80), available from Witco Corporation under the tradename VARONIC® LI S 80, as component B, and either the $C_{16}$ DMAPA-based quat (ternary system 3) or CTAC (ternary system 4) as component C. As with FIG. 1, it can be seen that the corresponding ternary phase system of the $C_{16}$ DMAPA-based quat is different from that of CTAC. As can be seen in FIG. 2, the introduction of a DMAPA unit into the quat molecule changes the interaction between the quat and the anionic surfactant and unexpectedly leads to a richer behavior. Some important aspects of the difference between the behavior of the $C_{16}$ DMAPA-based quat and CTAC discovered during these experiments and illustrated in FIG. 2 may be summarized as follows:
a. The $C_{16}$ DMAPA-based quat phase diagram has a much smaller two phase (2φ) region than that of the CTAC phase diagram.
b. The $C_{16}$ DMAPA-based quat phase diagram has one large viscous one phase (1φ) region.

The presence of the viscous region in the $C_{16}$ DMAPA-based quat ternary phase diagram is desirable for formulating products such as shampoos and body washes because it allows the formulators the freedom to choose viscosity. The results showed that the thickening property for clear formulations (ternary mixtures) provided by the $C_{16}$ DMAPA-based quat was unexpected and unique: this property was not found in the traditional quats.

FIG. 3

As shown in Table 2, FIG. 3 contains ternary systems 5 and 6 which each have sodium $C_{14-16}$ α-olefin sulfonate (AOS-PC), available from Rhone-Poulenc under the tradename RHODACAL® A-246-L, as component A, cocamidopropyl betaine (AMB 14), available from Witco Corporation under the tradename REWOTERIC® AMB 14, as component B, and either the $C_{16}$ DMAPA-based quat (ternary system 5) or CTAC (ternary system 6) as component C. As with FIGS. 1 and 2, it can be seen that the corresponding ternary phase system of the $C_{16}$ DMAPA-based is different from that of CTAC. As can be seen in FIG. 3, the introduction of the DMAPA unit into the quat molecule changes the interaction between the quat and the anionic surfactant and unexpectedly leads to a richer phase behavior. Some important aspects of the difference between the behavior of the $C_{16}$ DMAPA-based quat and CTAC discovered during these experiments and illustrated in FIG. 3 may be summarized as follows:
a. The $C_{16}$ DMAPA-based quat phase diagram has a much smaller two phase (2φ) region than that of the CTAC phase diagram.
b. The $C_{16}$ DMAPA-based quat phase diagram has one large gel phase region (very viscous) while the CTAC phase diagram has none.
c. The $C_{16}$ DMAPA-based quat gel phase is clear.
d. The large two phase (2φ) region in the CTAC phase diagram contrasts with the one gel phase and smaller two phase (2φ) region in the $C_{16}$ DMAPA-based quat phase diagram.

The presence of the gel phase region in the $C_{16}$ DMAPA-based quat ternary phase diagram is desirable for formulating products such as shampoos and body washes because it allows the formulators the freedom to choose desired viscosity.

As noted above, oppositely charged species can form complexes (or ion pairs) in dielectric media. Depending on the extent of this charge interaction, it may lead to the formation of a precipitate in strongly interacting systems. It is well-known in the art that quaternized ammonium surfactants strongly interact with anionic surfactants, leading to precipitation or dispersible complexes. In either case, clear systems cannot be formulated with these surfactants. It was unexpected to discover that a quaternized surfactant, for example, the $C_{16}$ DMAPA-based quat, can thicken the anionic/amphoteric systems while remaining clear; a property not seen in the traditional quats. The unexpected properties of the $C_{16}$ DMAPA-based quat can be seen in the phase diagrams shown in FIGS. 1 to 3.

Figure 4:
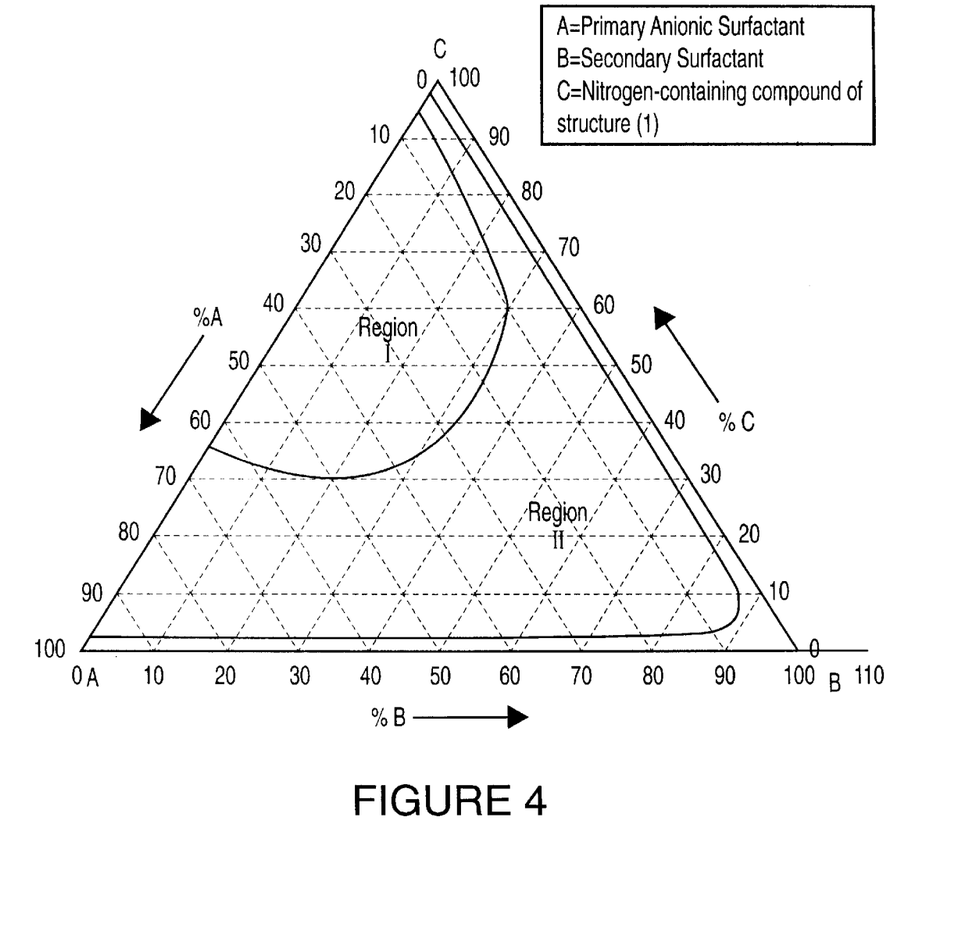
FIG. 4 is a model phase diagram illustrating the scope of the compositions of the present invention within the one phase and gel Region II, showing the ranges of components A, B, and C, wherein component A is the primary anionic surfactant, component B is the secondary surfactant, and component C is the nitrogen-containing compound of the structural formula (1).
Figure 5:
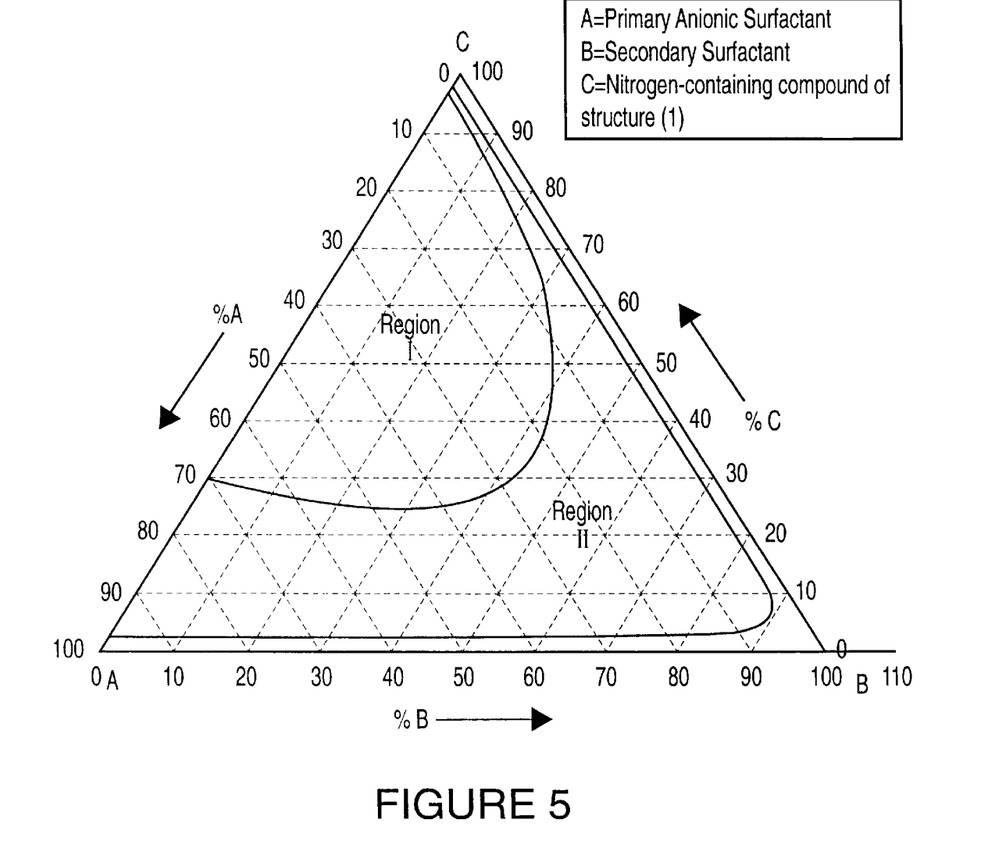
FIG. 5 is a model phase diagram illustrating the preferred scope of the compositions of the present invention within the one phase and gel Region II, showing the ranges of components A, B, and C, wherein component A is the primary anionic surfactant, component B is the secondary surfactant, and component C is the nitrogen-containing compound of the structural formula (1).

Two additional ternary phase diagrams are set forth in FIGS. 4 and 5 to illustrate the range of preferred compositions according to the instant invention. In a preferred embodiment of the present invention, the composition of the instant invention is defined as the one phase and gel regions (Region II) shown in FIG. 4, wherein the primary anionic surfactant (Component A), the secondary surfactant (Component B), and the nitrogen-containing compound (Component C) are present in respective ratios that define and are within the one-phase and gel regions (Region II). In another preferred embodiment of the invention, the composition of the instant invention is defined as the one phase and gel regions (Region II) shown in FIG. 5, wherein the primary anionic surfactant (Component A), the secondary surfactant (Component B), and the nitrogen-containing compound (Component C) are present in respective ratios that define and are within the one-phase gel regions (Region II). In each of FIGS. 4 and 5, Components A, B, and C are expressed as wt. % of actives.

The DMAPA-based quat compounds can be used alone or in mixtures in the formulations proposed, can be used in combination with other compounds or additives, or used as a formulation with other compounds or additives, depending on the intended use and the advantages and disadvantages attendant with each alternative application method. The compositions as described herein exhibit a number of desirable properties making them particularly suitable for formulation into commercial products such as conditioners and other personal care products as mentioned above. Most notably, the compositions are clear, i.e., transparent or translucent. This property can be realized at a variety of concentrations of active ingredient, with or even without special solvents or coupling agents. Other properties are realized as well. For instance, many of the compositions form a stable gel and exhibit advantageous stability, solubility, and freedom from objectionable color and odor.

It should be noted that the compositions of the present invention may be formulated without a solvent system, for example, as a solid or flake composition, or may be formulated to include water, propylene glycol, ethanol, isopropanol, diethylene glycol, or similar solvents or mixtures thereof, as a concentrate or more dilute form, depending on the application. Selection of a suitable solvent for a particular application is well-known to those of skill in the art.

It is understood that the compositions of the present invention can also contain appropriate aethestic additives for a given application, as would be known to those of skill in the art including, without limitation, perfumes, preservatives, silicones, and dyes. Moreover, additives may be used to adjust the chemical or physical properties of the formulation to a desired level. Thus, an acid, for example, citric acid, may be used to adjust the pH of the composition to an appropriate level and sodium chloride or other salt may be used to adjust the viscosity of the composition to a desired level. Usually the additives are present in small amounts, generally up to 2 wt. % each, to provide the desired properties. Other compounds or additives familiar to those of skill in the art and appropriate to a particular use may also be used with or formulated with the composition of the present invention.

It is also understood that many of the examples and claims presented include components that are salts, that is, they include an anion and a cation. It is understood by those of skill in the art that the identity anion or cation of a given compound may not be crucial in the activity of the compound for a given purpose (that is, it may constitute a spectator ion) and an appropriate substitute may be made therefor. Thus, with regard to the DMAPA-based quats, the counteranion may be, for example, chloride, bromide, methyl sulfate, ethyl sulfate, or salicylate. Similarly, the sodium ion present in many of the primary anionic surfactants claimed and presented in the examples above may be replaced by other cations, such as potassium ion or ammonium ion, without appreciably affecting the performance of the primary anionic surfactant. Furthermore, with regard to the salt component that may be added to the composition or subsequently added to the composition to obtain a desired viscosity, the term "salt" is intended to cover all of the compounds known to those of skill in the art to be equivalent to those mentioned herein. Thus, it is understood that such ions may be substituted by any other ion which is not significantly deleterious to the desired chemical or physical properties of the overall compound in its intended use herein. It is therefore understood that such ion substitution is well-known in the art and all such possibilities and equivalents are intended to be embraced within the appended claims.

Sample Formulations (L–T) demonstrate the compatibility of specific DMAPA-based quaternaries with an anionic resin and silicon. In addition these formulations containing an anionic resin give superior performance and are clear. These formulations are prepared in the same manner as previously described for formulations A–K.

| Ingredients | Wt. % |
| --- | --- |
| FORMULATION L | |
| Sodium Laureth Sulfate-2 (26.5%) | 50.0% |
| Disodium Laureth Sulfosuccinate (40%) | 7.0 |
| Cocamidopropyl betaine (35%) | 6.0 |
| Glycerine (USP, 99.7%) | 3.0 |
| Monobutyl Ester of Poly(Methyl Vinyl Ether/Maleic Acid) (GANREZ A-425, ISP) | 0.8 |
| Palmitamidopropyltrimonium Chloride (30%) (VARISOFT ® PATC) | 3.0 |
| Water | 29.0 |
| NaCl | 1.2 |
| FORMULATION M | |
| Sodium Laureth Sulfate-2 (26.5%) | 30.0% |
| Disodium Laureth Sulfosuccinate (40%) | 5.0 |
| Cocamidopropyl betaine (35%) | 4.0 |
| Glycerine (USP, 99.7%) | 2.0 |
| Monobutyl Ester of Poly(Methyl Vinyl Ether/Maleic Acid) (GANREZ A-425, ISP) | 0.7 |
| Palmitamidopropyltrimonium Chloride (30%) (VARISOFT ® PATC) | 5.0 |
| Water | 52.3 |
| NaCl | 1.0 |
| FORMULATION N | |
| Sodium Laureth Sulfate-2 (26.5%) | 29.9% |
| Disodium Laureth Sulfosuccinate (40%) | 5.0 |
| Cocamidopropyl betaine (35%) | 4.0 |
| Glycerine (USP, 99.7%) | 2.0 |
| Vinylpyrrolidone Dimethylaminopropylmethacrylamide Copolymer (STYLEZE CC-10) | 1.0 |
| Palmitamidopropyltrimonium Chloride (30%) (VARISOFT ® PATC) | 5.0 |
| Water | 52.1 |
| NaCl | 1.0 |
| FORMULATION O | |
| Sodium Laureth Sulfate-2 (26.5%) | 29.8% |
| Disodium Laureth Sulfosuccinate (40%) | 5.0 |
| Cocamidopropyl betaine (35%) | 4.0 |
| Glycerine (USP, 99.7%) | 2.0 |
| Vinylpyrrolidone Dimethylaminopropylmethacrylamide Copolymer (STYLEZE CC-10) | 1.0 |
| Palmitamidopropyltrimonium Chloride (30%) (VARISOFT ® PATC) | 5.0 |
| Water | 51.9 |
| Silicone (EO + PO, SILWET 7001) | 0.5 |
| NaCl | 1.0 |
| FORMULATION P | |
| Sodium Laureth Sulfate-2 (26.5%) | 29.6% |
| Disodium Laureth Sulfosuccinate (40%) | 4.9 |
| Cocamidopropyl betaine (35%) | 3.9 |
| Glycerine (USP, 99.7%) | 2.0 |
| Vinylpyrrolidone Dimethylaminopropylmethacrylamide Copolymer (STYLEZE CC-10) | 1.0 |
| Palmitamidopropyltrimonium Chloride (30%) (VARISOFT ® PATC) | 4.9 |
| Water | 52.6 |
| Silicone (amino derived, SILWET A-843) | 1.0 |
| NaCl | 1.0 |
| FORMULATION Q | |
| Ammonium Lauryl Sulfate | 30.0% |
| Disodium Laureth Sulfosuccinate (40%) | 5.0 |
| Cocamidopropyl betaine (35%) | 4.0 |
| Glycerine (USP, 99.7%) | 2.0 |
| MVE/MA Copolymer Crosslinked with 1,9-Decadiene (STABILEZE 06, ISP) | 0.4 |
| Palmitamidopropyltrimonium Chloride (30%) (VARISOFT ® PATC) | 5.0 |
| Water | 51.2 |

| Ingredients | Wt. % |
|---|---|
| Dimethicone (SILWET L-45) | 2.0 |
| NaCl | 0.4 |
| FORMULATION R | |
| Ammonium Lauryl Sulfate | 30.0% |
| Disodium Laureth Sulfosuccinate (40%) | 5.0 |
| Cocamidopropyl betaine (35%) | 4.0 |
| Glycerine (USP, 99.7%) | 2.0 |
| MVE/MA Copolymer Crosslinked with 1,9-Decadiene (STABILEZE 06, ISP) | 0.4 |
| Palmitamidopropyltrimonium Chloride (30%) (VARISOFT ® PATC) | 5.0 |
| Water | 51.2 |
| Silicone (amino, SILWET A-843) | 2.0 |
| NaCl | 0.4 |
| FORMULATION S | |
| Ammonium Lauryl Sulfate | 30.0% |
| Disodium Laureth Sulfosuccinate (40%) | 5.0 |
| Cocamidopropyl betaine (35%) | 4.0 |
| Glycerine (USP, 99.7%) | 2.0 |
| MVE/MA Copolymer Crosslinked with 1,9-Decadiene (STABILEZE 06, ISP) | 0.4 |
| Palmitamidopropyltrimonium Chloride (30%) (VARISOFT ® PATC) | 5.0 |
| Water | 51.2 |
| Dimethicone Gum (100,000 cps) | 2.0 |
| NaCl | 0.4 |
| FORMULATION T | |
| Ammonium Lauryl Sulfate | 30.0% |
| Disodium Laureth Sulfosuccinate (40%) | 5.0 |
| Cocamidopropyl betaine (35%) | 4.0 |
| Glycerine (USP, 99.7%) | 2.0 |
| MVE/MA Copolymer Crosslinked with 1,9-Decadiene (STABILEZE 06, ISP) | 0.4 |
| Palmitamidopropyltrimonium Chloride (30%) (VARISOFT ® PATC) | 5.0 |
| Water | 51.2 |
| Silicone (EO + PO, SILWET 7001) | 2.0 |
| NaCl | 0.4 |

Formulations U and V were prepared using identical ingredients with the exception that Formulation U contained 1.8% palmitamidopropyltrimonium chloride (VARISOFT® PATC) and Formulation V contained 1.8% cocamidopropyl betaine. These two formulations are summarized in Table 3 below.

What is of most interest in these formulations is the difference in aesthetics (viscosity, skin feel, etc.) and a reduction in irritation. VARISOFT® PATC by itself is an irritant in a Red Blood Cell Test (RBC, a standard in-vitro method for determining irritation potential). When the formulation contains VARISOFT® PATC, an actual improvement of the irritation profiles of the other ingredients is observed; a definite synergism. Formulation U would be thus classified as a moderate irritant, which is a significant improvement over Formulation V, which would be classified as an irritant. The above synergism of Formulation U is not seen with other cationic quats.

Additionally, the viscosity of the two formulations was quite different. With no additional salt added, the viscosity of Formulation U was 1300 cps; the viscosity of Formulation V, on the other hand, was only 44.2 cps. The Ross-Miles foam heights were the same for both formulations (Standard ASTM testing method for surfactants).

Sheet 1

| Ingredients | Formula U | | | Formula V | | |
|---|---|---|---|---|---|---|
| | Wt. % | Mass | % act | Wt. % | Mass | % act |
| Sodium Laureth-2 Sulfate | 9.98 | 84.98 | 2.6 | 10.04 | 100.7 | 2.6 |
| Disodium Laureth Sulfosuccunate | 12.47 | 106.22 | 6.2 | 12.51 | 125.44 | 6.2 |
| PEG-200 Hydrogenated Glyceryl Palmitate and PEG-7 Glyceryl Cocoate | 4.99 | 42.48 | 3.5 | 5.07 | 50.84 | 3.5 |
| Sodium Cocoamphoacetate | 9.98 | 85.01 | 4.0 | 10.03 | 100.63 | 4.0 |
| Palmitamidopropyltrumonium Chloride | 2.99 | 25.45 | 1.8 | | | |
| Cocamidopropyl Betaine | | | | 5.01 | 50.22 | 1.8 |
| Water | 59.60 | 507.7 | | 57.34 | 575.09 | |
| | | 851.84 | | | 1002.92 | |

As noted above, the examples provided are intended to further describe the aspects of the present invention. The examples are illustrative only and are not to be construed as limiting the scope of that which is regarded as the invention. Therefore, the scope of the present invention is only to be limited by the following claims and the equivalents thereto.

What is claimed is:

1. A clear composition formulated from ingredients comprising:
   a primary anionic surfactant; and
   a nitrogen-containing compound of the structural formula:

wherein
R is a saturated or unsaturated, linear, branched or cyclic alkyl or aryl group containing 12 to 22 carbon atoms that is unsubstituted, with the proviso that R contains at least 80% of a single chain length and R is not lanolin, wheat germ or another natural broad-based chain distribution oil;

$R_1$ is a saturated or unsaturated, linear, branched or cyclic alkylene group containing 1 to 6 carbon atoms and 0 to 3 hydroxyl groups;

$R_2$ is selected from the group consisting of hydrogen, methyl, ethyl, and benzyl; and $A^-$ is a monovalent anion, wherein the weight ratio of said primary anionic surfactant to said nitrogen-containing compound is from 12:1 to 1:12.

2. The clear composition of claim 1, wherein said weight ratio of said primary anionic surfactant to said nitrogen-containing compound is from 8:1 to 1:8.

3. The clear composition of claim 1, wherein the primary anionic surfactant is selected from the group consisting of ammonium lauryl sulfate, sodium lauryl sulfate, an α-olefin sulfonate, ammonium laureth sulfate (2 or 3 moles EO), sodium laureth sulfate (2 or 3 moles EO), sodium myristyl sulfate, sodium myristeth sulfate (1–4 moles EO), TEA-dodecylbenzene sulfonate, TEA lauryl sulfate, ammonium pareth sulfate, sodium pareth sulfate, sodium oleth sulfate, linear alkyl benzene sulfonate, and mixtures thereof.

4. The clear composition of claim 1, wherein the primary anionic surfactant comprises between about 1 wt. % to about 50 wt. % of the composition.

5. The clear composition of claim 1, further comprising a secondary surfactant, said secondary surfactant being present in an amount such that the weight ratio of said secondary surfactant to said nitrogen-containing compound is from 6:1 to 1:6.

6. The clear composition of claim 5, wherein said weight ratio of said secondary surfactant to said nitrogen-containing compound is from 3:1 to 1:3.

7. The clear composition of claim 5, wherein the secondary surfactant is selected from the group consisting of cocamidopropyl betaine, lauramidopropyl betaine, ricinoleamidopropyl betaine, myristamidopropyl betaine, palmamidopropyl betaine, stearamidopropyl betaine, behenamidopropyl betaine, erucamidopropyl betaine, cocamidopropyl hydroxysultaine, myristamidopropyl hydroxysultaine, palmamidopropyl hydroxysultaine, stearamidopropyl hydroxysultaine, behenamidopropyl hydroxysultaine, erucamidopropyl hydroxysultaine, disodium lauroamphodiacetate, disodium erucamphodiacetate, sodium lauryl amphoacetate, sodium cocamphoacetate, sodium cocoamphopropionate, sodium laurylamphopropionate, disodium lauroamphodipropionate, sodium lauryl sulfosuccinate, disodium laureth sulfosuccinate, cocobetaine, laurylbetaine, myristylbetaine, stearylbetaine, behenylbetaine, PEG 1-300 glyceryl cocoate, PEG 1-300 glyceryl tallowate, PEG 1-500 hydrogenated glyceryl palmitate, coco-glucoside, lauryl glucoside, decyl glucoside, sodium xylene sulfonate, and mixtures thereof.

8. The clear composition of claim 5, wherein the secondary surfactant comprises between about 0.1 wt. % to about 50 wt. % (expressed as actives) of the total amount of said primary anionic surfactant, said secondary surfactant and said nitrogen-containing compound, expressed as actives.

9. The clear composition of claim 8, wherein the secondary surfactant comprises between 0.5 wt. % to about 10 wt. % (expressed as actives) of the total amount of said primary anionic surfactant, said secondary surfactant and said nitrogen-containing compound, expressed as actives.

10. The clear composition of claim 1, wherein the nitrogen-containing compound comprises between about 0.1 wt. % to about 50 wt. % (expressed as actives) of the total amount of components in said composition, expressed as actives.

11. The clear composition of claim 10, wherein the nitrogen-containing compound comprises between 0.5 wt. % to about 20 wt. % (expressed as actives) of the total amount of components in said composition, expressed as actives.

12. The clear composition of claim 11, wherein the nitrogen-containing compound comprises between about 0.75 wt. % to about 10 wt. % (expressed as actives) of the total amount of components in said composition, expressed as actives.

13. The clear composition of claim 1, wherein $R_1$ is —$CH_2CH_2CH_2$—.

14. The clear composition of claim 1, wherein R is a saturated, linear alkyl group containing 12 to 22 carbon atoms that is unsubstituted and saturated.

15. The clear composition of claim 1, wherein $R_2$ is methyl.

16. The clear composition of claim 1, further comprising a salt.

17. The clear composition of claim 16, wherein the salt is selected from the group consisting of sodium chloride, potassium chloride, calcium chloride, magnesium chloride, ammonium chloride, sodium bromide, potassium bromide, calcium bromide, magnesium bromide, ammonium bromide, sodium iodide, potassium iodide, calcium iodide, magnesium iodide, ammonium iodide, sodium acetate, potassium acetate, and mixtures thereof.

18. The clear composition of claim 15, wherein $R_1$ is —$CH_2CH_2CH_2$—.

19. The clear composition of claim 5, further comprising a resin.

20. The clear composition of claim 19, wherein said resin is a maleic acid-containing copolymer with anionic charges.

21. The clear composition of claim 19, wherein the resin comprises between about 0.01 wt. % to about 3.0 wt. % (expressed as actives) of the total amount of all components in said composition, expressed as actives.

22. The clear composition of claim 21, wherein the resin comprises between about 0.025 wt. % to about 1.5 wt. % (expressed as actives) of the total amount of all components in said composition, expressed as actives.

23. The clear composition of claim 1, further comprising a resin.

24. The clear composition of claim 23, wherein said resin is a maleic acid-containing copolymer with anionic charges.

25. The clear composition of claim 23, wherein the resin comprises between about 0.01 wt. % to about 3.0 wt. % (expressed as actives) of the total amount of all components in said composition, expressed as actives.

26. The clear composition of claim 25, wherein the resin comprises between about 0.025 wt. % to about 1.5 wt. % (expressed as actives) of the total amount of all components in said composition, expressed as actives.

27. A formulation comprising at least palmitamidopropyltrimonium chloride and a primary anionic surfactant wherein said formulation mitigates skin-irritation, said primary anionic surfactant and palmitamidopropyltrimonium chloride are present in a concentration to provide a weight ratio of said anionic surfactant to palmitamidopropyltrimonium chloride of from 3:1 to 1:3.

* * * * *